United States Patent [19]

Schneider et al.

[11] Patent Number: 4,583,980
[45] Date of Patent: Apr. 22, 1986

[54] SANITARY HYGIENE PRODUCTS HAVING ODOR-PREVENTING PROPERTIES

[75] Inventors: Werner Schneider, Krefeld-Bockum; Scarlet Sustmann, Münster, both of Fed. Rep. of Germany

[73] Assignee: Henkel Kommanditgesellschaft auf Aktien, Düsseldorf-Holthausen, Fed. Rep. of Germany

[21] Appl. No.: 691,715

[22] Filed: Jan. 14, 1985

Related U.S. Application Data

[63] Continuation of Ser. No. 524,829, Aug. 19, 1983, abandoned, which is a continuation of Ser. No. 288,787, Jul. 31, 1981, abandoned.

[30] Foreign Application Priority Data

Aug. 16, 1980 [DE] Fed. Rep. of Germany ....... 3030920

[51] Int. Cl.$^4$ ............................................. A61F 13/16
[52] U.S. Cl. .................................................. 604/359
[58] Field of Search ............... 604/359, 378, 360, 374, 604/358; 424/28, 47, 76

[56] References Cited

U.S. PATENT DOCUMENTS

| | | | |
|---|---|---|---|
| 1,950,957 | 3/1934 | Wilhelm | 424/28 |
| 2,542,909 | 2/1951 | DeWet | 424/25 |
| 3,024,207 | 3/1962 | Shaw et al. | 521/28 |
| 3,124,135 | 3/1964 | Olson | 604/378 |
| 3,172,817 | 3/1965 | Leupold et al. | 424/28 |
| 3,490,454 | 1/1970 | Goldfarb et al. | 604/359 |
| 3,525,338 | 8/1970 | Bernardin | 604/374 |
| 3,691,271 | 9/1972 | Charle et al. | 424/28 |
| 3,804,094 | 4/1974 | Manoussos et al. | 604/359 |
| 4,010,253 | 3/1977 | Reese et al. | 424/47 |
| 4,059,114 | 11/1977 | Richards | 604/359 |

*Primary Examiner*—John D. Yasko
*Attorney, Agent, or Firm*—Hammond & Littell, Weissenberger & Dippert

[57] ABSTRACT

This invention is directed to sanitary hygiene products. More particularly, this invention is directed to sanitary hygiene products for the absorption of secretions containing urine and/or blood which contains in an absorption layer an odor-preventing amount of one or more esters of citric acid and/or acetylcitric acid with aliphatic alcohols with from 1 to 6 carbon atoms or alicyclic alcohols with from 4 to 6 carbon atoms, as an odor-preventing substance.

4 Claims, 1 Drawing Figure

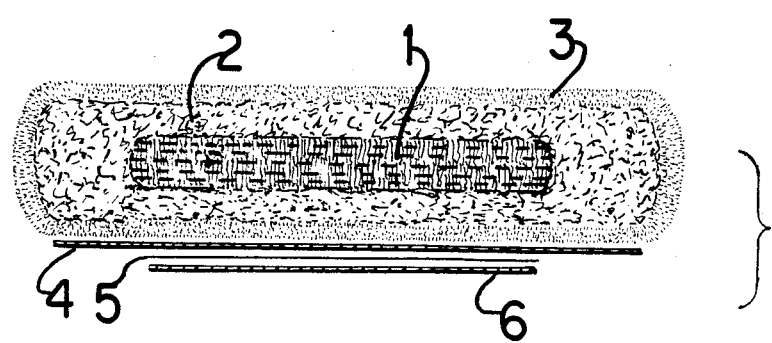

SANITARY HYGIENE PRODUCTS HAVING ODOR-PREVENTING PROPERTIES

CROSS REFERENCE TO RELATED APPLICATIONS

This application is a continuation of co-pending U.S. patent application Ser. No. 524,829, filed Aug. 19 1983, now abandoned which in turn is a continuation of U.S. patent application Ser. No. 288,787, filed July 31, 198, now abandoned.

FIELD OF THE INVENTION

This invention is directed to sanitary hygiene products. More particularly, this invention is directed to sanitary hygiene products for the absorption of secretions containing urine and/or blood which have an absorbent layer containing esters of citric acid and/or acetylcitric acid as odor-preventing substance.

BACKGROUND OF THE INVENTION

The impregation of sanitary hygiene products with disinfectants, medicaments, or fragrances to prevent as much as possible the occurrence of unpleasant odor, is well known. For this purpose, phenols, mercuric chloride, and sulfurous acid as well as various bactericides and fungicides such as chloramine, Actamer ® (2,2'-thiobis-(4,6-dichlorophenol, available from Monsanto Co.), hexachlorophene, bis-(tri-n-alkyl-tin)sulfosalicylates, and phenyl-mercury salts, and the like, have been added to absorbent layers of the sanitary hygiene products. In addition, it has been known to treat such absorbent layers successively with sodium acetate and sodium bisulfate. Such additions or treatments suppress the formation of unpleasant odors to a certain degree since they kill the microorganisms responsible for the generation of the odors. However, this suppression of unpleasant odors by the killing of the microorganisms responsible for the decomposition of blood and urine is associated with a greater or lesser damage of the body's own cutaneous and vaginal flora. In addition, occasional intolerance, photosensitization, and toxic side effects of varying degree occur with the use of some agents and prevent their application on a broad base. Consequently, the search has continued for substances that prevent the formation of unpleasant odors without causing harmful side-effects.

OBJECTS OF THE INVENTION

It is an object of the invention to provide sanitary hygiene products having odor-preventing properties.

It is also an object of the invention to provide sanitary hygiene products having an absorbent layer wherein the absorbent layer is treated with a substance that does not cause harmful side-effects.

It is a further object of the invention to provide sanitary hygiene products having absorbent layers containing esters of citric acid and/or acetylcitric acid with aliphatic alcohols of from 1 to 6 carbon atoms or alicyclic alcohols of from 4 to 6 carbon atoms.

These and other objects of the invention will become more apparent in the discussion below.

DETAILED DESCRIPTION OF THE DRAWING

The FIGURE represents a cross-sectional view of one embodiment of a sanitary hygiene product according to the invention.

DETAILED DESCRIPTION OF THE INVENTION

Suitable substances useful in sanitary hygiene products which inhibit the formation of unpleasant odors and do not cause the harmful side-effects associated with the prior art, have now been found. According to Applicant's invention, sanitary hygiene products for the absorption of urine and/or blood have an absorbent layer that contains esters of citric acid and/or acetylcitric acid with aliphatic alcohols of from 1 to 6 carbon atoms or alicyclic alcohols of from 4 to 6 carbon atoms.

The applicable thrust of the invention, that is, the products to which the invention is directed, comprises sanitary hygiene products having an absorbent layer to absorb urine and/or blood, such as diapers, panty shields sanitary napkins, or tampons. The absorbent layer, which is a primary aspect of such sanitary hygiene products, comprises a suitable absorbent fibrous material normally used in such products. For example, the fibrous material may consist of spun wool, cotton, chemical cellulose fibers, synthetic textile fibers, fleece cloth, as well as expanding polymers such as modified starch, modified cellulose, or absorbent synthetic particles. The absorbent material is typically either glued to paper or other laminates or embedded in netting, non-woven or fleece cloth, but also expanding polymers such as modified starch, modified cellulose or absorbent synthetic particles, which are glued to paper or other laminates, or embedded in netting, non-woven or fleece cloth, of textile widths, for easier handling.

For an effective prevention of the local decomposition of the secretions taken up in the absorbent layer, it is important that the absorbent layer is penetrated as uniformly as possible by the esters of citric acid and/or acetylcitric acid. The requirement of as uniform a penetration of the absorption layer as possible is readily met by the products to be used according to the invention, since, as liquids, they can be applied in a very fine distribution, for example, as fog droplets or from the vapor phase. An additional advantage, which results from the liquid state of the products to be used according to the invention, is their ready miscibility with fragrances, which may also be added, if desired.

The esters of citric acid to be used according to the invention can be prepared by a known method by azeotropic esterification of citric acid with the respective alcohol, as described, for example, for the triethyl ester of citric acid in U.S. Pat. No. 2,076,111, incorporated herein by reference. The acetylcitric acid ester to be used according to the invention can be prepared by reaction of the respective citric acid ester with acetylchloride, as described for the triethyl ester of acetylcitric acid by Wislincenus in Liebigs Annalen der Chemie 129:192, incorporated herein by reference, or by reaction of the respective citric acid ester with acetic anydride, as also described for the triethyl ester of acetylcitric acid in U.S. Pat. No. 2,445,911, incorporated herein by reference.

Alcohols suitable for the esterification include, for example, methanol, ethanol, propanol, isopropanol, 1-butanol, 2-butanol, 2-methyl-1-propanol, 2-methyl-2-propanol, 2-methyl-1-butanol, 2-methyl-4-butanol, n-hexanol, ethylene glycol, proplyene glycol, trimethylene glycol, hexamethylene glycol, glycerol, erythritol, sorbitol, and cyclohexanol.

Most important among the esters of citric acid as well as of acetylcitric acid to be used according to the invention are the respective triesters. And, among the respective triesters, the triethyl ester of citric acid is distinguished by having the strongest odor-preventing effect as well as the best suitability for practical application.

The triethyl ester of citric acid is accepted as food additive and thus can be considered harmless; even overdoses cannot result in skin irritations or other intolerance reactions. Since the triethyl citrate is not antibacterially active, no medically undesirable disturbance of the body's own cutaneous and vaginal flora can occur through its use.

As explained above, a penetration as uniform as possible of the absorbent layer by the substances according to the invention is a prerequisite for the absence of local decomposition reactions and thus undesirable formation of odor. Completely homogenous impregnation can be achieved, for example, by a procedure in which the absorbent material, or a prototype finished product, that is, an assembled product, is placed in an evacuated chamber and, after a vacuum is produced, the citric acid ester or acetylcitric acid ester is vaporized at elevated temperature until its saturation pressure is reached. During this process, the material is uniformly penetrated by the citric acid ester or acetylcitric acid ester, and the concentration in the textile or paperlike materials are in equilibrium with the vapor phase. The amount of citric acid ester or acetylcitric acid ester to be applied can be exactly controlled in this process by the vaporization temperature and the vacuum. The triethyl ester of citric acid has proven to be the most suitable for impregnation by this method. Local decomposition of secretions containing blood and/or urine are significantly inhibited in a sanitary hygiene product completely homogeneously impregnated in this manner.

Since the triethyl ester of citric acid itself is chemically relatively inert and has no odor, it can be mixed easily with perfume oils without any effect on the odor quality. This is particularly advantageous when the simultaneous perfuming of the sanitary hygiene product is desired. In such a case, the triethyl citrate and the perfume oil can be applied as a mixture without any difficulties. For this purpose, the absorbent material is sent through a chamber in which the mixture of triethyl citrate and perfume oil is finely atomized so that the absorbing materials are evenly wetted due to the small size of the droplets. An especially fine distribution of the mixture of triethyl citrate and perfume oil can be achieved by the application of an electrical field to the atomization chamber.

To perhaps better appreciate the invention, reference is made to an embodiment of the invention, namely, a panty shield sanitary napkin, represented in the Figure. The highly absorbent layer 1 has been homogeneously impregnated with triethyl citrate and, optionally, perfume oil, and absorbent layer 1 is surrounded by a layer 2 of staple rayon fiber as a batt or fluff that has not been impregnated. The outer perimeter of layer 2 is in turn covered by a layer 3 of nonwoven cloth or fleece cloth. The portion of the outer surface of layer 3 intended to be away from the body, and thus in contact with clothing, is covered with a foil or protective means 4 comprised of suitable synthetic material or water-proof paper, that is intended to protect clothing. Protective means 4 is covered by one or more adhesive strips 5 and then silicone paper 6. When the panty liner sanitary napkin of the Figure is put in place for use, the silicone paper 6 is removed from the adhesive strips 5 so that the napkin adheres to the panty.

The absorbent layer 1 contains highly absorbent polymers with strong absorptive capacity, for example, starch graft polymers, which are well wetted by the triethyl citrate without swelling. This wetting of the polymer by the triethyl citrate does not, however, in any way diminish the swelling capacity of the absorptive substance. The described design offers two advantages: First, a diffusion of the triethyl citrate into the foil protecting the clothing and to the adhesive strip is prevented by the location of the highly absorbent absorption layer wetted with triethyl citrate; and second, the odor-preventing triethyl citrate is located exactly in the area where the secretions are taken up since in the example described the secretion is absorbed almost exclusively in the impregnated, highly absorbent layer, which takes up the liquid and retains it. The prevention of diffusion is desirable since a wavy deformation of the foil and a reduction of the adhesive capacity can occur otherwise. The described substrate is finished by rolling or turning under and then it is wrapped individually in cellophane or an opaque foil.

The following examples are intended to illustrate the invention and should not be construed as limiting the invention thereto.

EXAMPLES

Determination of the Inhibitory Effect of Triethyl Ester of Citric Acid on the Decomposition of Urine

(a) Odor Test

Four grams of milled wood pulp (fluff) were sprayed with 0.5 gm or 1.5 gm of triethyl citrate, respectively, and mixed well. Then, 25 ml of fresh urine were added to the fluff treated in the above manner as well as to an equal amount of untreated fluff. The samples were incubated for 14 hours at 37° C. in a container that was closed with a cotton wad that allowed air to penetrate. Then, the samples were submitted to five different persons for an odor test. The labelling of the samples did not allow any conclusions about possible additions. The sample without any addition of triethyl citrate was identified each time in five independent test series by all five test persons as having by far the most unpleasant smell. The difference between the sample with untreated fluff and the sample with fluff plus 1.5 gm of triethyl citrate was perceived as the greatest. The concentration of triethyl citrate in this sample was 0,375 g per 1 g stuff. If one assumes a maximum amount of 3 ml of urine per panty shield (approximately the holding capacity of a panty shield containing 1 g of absorbent material), an amount of $(0,375/25) \times 3$ g, that is 45 mg of triethyl citrate per panty shield, thus would yield an unequivocal result.

(b) Inhibition of Alalkinization

Ammonia is released due to the urease activity during the decomposition of urine, which release causes a shift in the initially acid pH to the basic side. Here, 4 gm of milled wood pulp (fluff) or 4 gm of cotton wadding were sprayed with 0.5 gm or 1.5 gm triethyl citrate, respectively, and mixed well for the purpose of the test. Then, 25 ml of fresh urine were added to the absorption material treated in this manner as well as to an equal amount of untreated absorption material. These samples and one urine sample without the addition of absorption material were incubated at 37° C. for 14 hours in a container stoppered with a cotton wad that permitted air to penetrate. Then, the pH of each sample was determined and compared with the pH measured before the incubation. The pH values obtained in the tests are recorded in the table below.

TABLE

| | | | pH Values of Urine in Absorbent Layer (aged) | | | | | |
|---|---|---|---|---|---|---|---|---|
| Example | Urine Sample (initially) (pH) | Urine Sample (aged) (pH) | Absorbent Layer of Fluff | Absorbent Layer of Cotton Wadding | Absorbent Layer of Fluff + 0.5 gm TEC* | Absorbent Layer of Cotton Wadding + 0.5 gm TEC* | Absorbent Layer of Fluff + 1.5 gm TEC* | Absorbent Layer of Cotton Wadding + 1.5 gm TEC* |
| 1 | 6.0 | 8.7 | 7.7 | — | 7.2 | — | 6.7 | — |
| 2 | 6.7 | 8.5 | 7.4 | — | 7.0 | — | 6.9 | — |
| 3 | 6.3 | 7.6 | — | 7.4 | — | 6.6 | — | 6.6 |

*Triethyl citrate

As can be seen from the table above, the alkalinization was suppressed in all cases by the addition of triethyl citrate. Differences of from 0.5 to 1.0 pH unit were observed. In Example 2, the pH of the fresh urine was elevated by the addition of aged urine. The table also shows that the addition of fluff or cotton wadding alone leads to a reduction of the urease activity.

As is apparent from the tests above, decomposition and thus the developing of unpleasant odors can be largely prevented by the use of triethyl citrate in the sanitary hygiene products soiled with urine.

Additional tests were carried out using a procedure analogous to that of odor test (2), but using an aqueous solution of pig's blood diluted 1:1 instead of urine. Triethyl citrate demonstrated a relatively complete suppression of unpleasant odors in these tests.

The use of esters of citric acid and/or acetylcitric acid in anhydrous cosmetic preparations for the suppression of body odor is already known from, for example, U.S. Pat. No. 4,010,253. However, the fact that a compound without antibacterial activity reduces the decomposition of perspiration upon application to the skin does not teach or suggest that this compound largely prevents the decomposition of secretions containing blood and urine and the formation of unpleasant odors when it is used as an additive to textile and paper-like absorption materials for such secretions.

The preceding specific embodiments are illustrative of the practice of the invention. It is to be understood, however, that other expedients known to those skilled in the art or disclosed herein, may be employed without departing from the spirit of the invention or the scope of the appended claims.

We claims:

1. A sanitary hygiene product for the absorption of secretions containing urine and/or blood which contains in an absorption layer an odor-preventing amount of one or more esters of citric acid and/or acetylcitric acid with aliphatic alcohols with from 1 to 6 carbon atoms or alicyclic alcohols of from 4 to 6 carbon atoms, as an odor-preventing substance, the absorption layer being arranged in the center of the product and being surrounded by a layer of cotton wadding or milled staple rayon fluff.

2. The sanitary hygiene product of claim 1, wherein the absorption layer contains triethyl citrate.

3. The sanitary hygiene product of claim 1, wherein the absorption layer also contains perfume oil.

4. The sanitary hygiene product of claim 1, wherein the absorption layer comprises a highly absorbent polymer with strong absorptive capacity and said absorption layer is impregnated with an ester of citric acid and/or acetylcitric acid.

* * * * *